United States Patent
Ueno et al.

(10) Patent No.: US 9,398,849 B2
(45) Date of Patent: Jul. 26, 2016

(54) OPHTHALMIC APPARATUS, ANALYSIS PROGRAM, OPTIC MEDIA OPACITY ACQUIRING METHOD, AND FLUORESCENCE INTENSITY ACQUIRING METHOD

(71) Applicant: NIDEK CO., LTD., Gamagori-shi, Aichi (JP)

(72) Inventors: Tokio Ueno, Nagoya (JP); Katsuyasu Mizuno, Gamagori (JP); Junichi Akita, Okazaki (JP)

(73) Assignee: NIDEK CO., LTD., Gamagori-shi (JP)

( * ) Notice: Subject to any disclaimer, the term of this patent is extended or adjusted under 35 U.S.C. 154(b) by 308 days.

(21) Appl. No.: 14/266,095

(22) Filed: Apr. 30, 2014

(65) Prior Publication Data
US 2014/0333896 A1   Nov. 13, 2014

(30) Foreign Application Priority Data

May 1, 2013   (JP) .................................. 2013-096180
Sep. 27, 2013 (JP) .................................. 2013-201984

(51) Int. Cl.
| | |
|---|---|
| A61B 3/10 | (2006.01) |
| A61B 3/00 | (2006.01) |
| A61B 3/14 | (2006.01) |
| A61B 3/12 | (2006.01) |

(52) U.S. Cl.
CPC ... *A61B 3/12* (2013.01); *A61B 3/10* (2013.01); *A61B 3/1025* (2013.01)

(58) Field of Classification Search
USPC .......................................... 359/206, 221, 246
See application file for complete search history.

(56) References Cited

U.S. PATENT DOCUMENTS

2006/0203194 A1   9/2006   Suzuki

FOREIGN PATENT DOCUMENTS

JP   A-2006-247076   9/2006

*Primary Examiner* — Jack Dinh
(74) *Attorney, Agent, or Firm* — Oliff PLC

(57) ABSTRACT

An ophthalmic apparatus includes: a light projecting optical system to project light to each point on a fundus of an examinee's eye; a light receiving optical system including a light receiving element to receive light from the fundus emitted from each point on the fundus resulting from the light projected from the light projecting optical system; and a controller for controlling the ophthalmic apparatus, wherein the controller is configured to: acquire intensity information representing intensity of the light from the fundus corresponding to each point on the fundus based on a result of received light of the light receiving element; and analyze a degree of opacity in an optic media of the examinee's eye based on the intensity information.

10 Claims, 8 Drawing Sheets

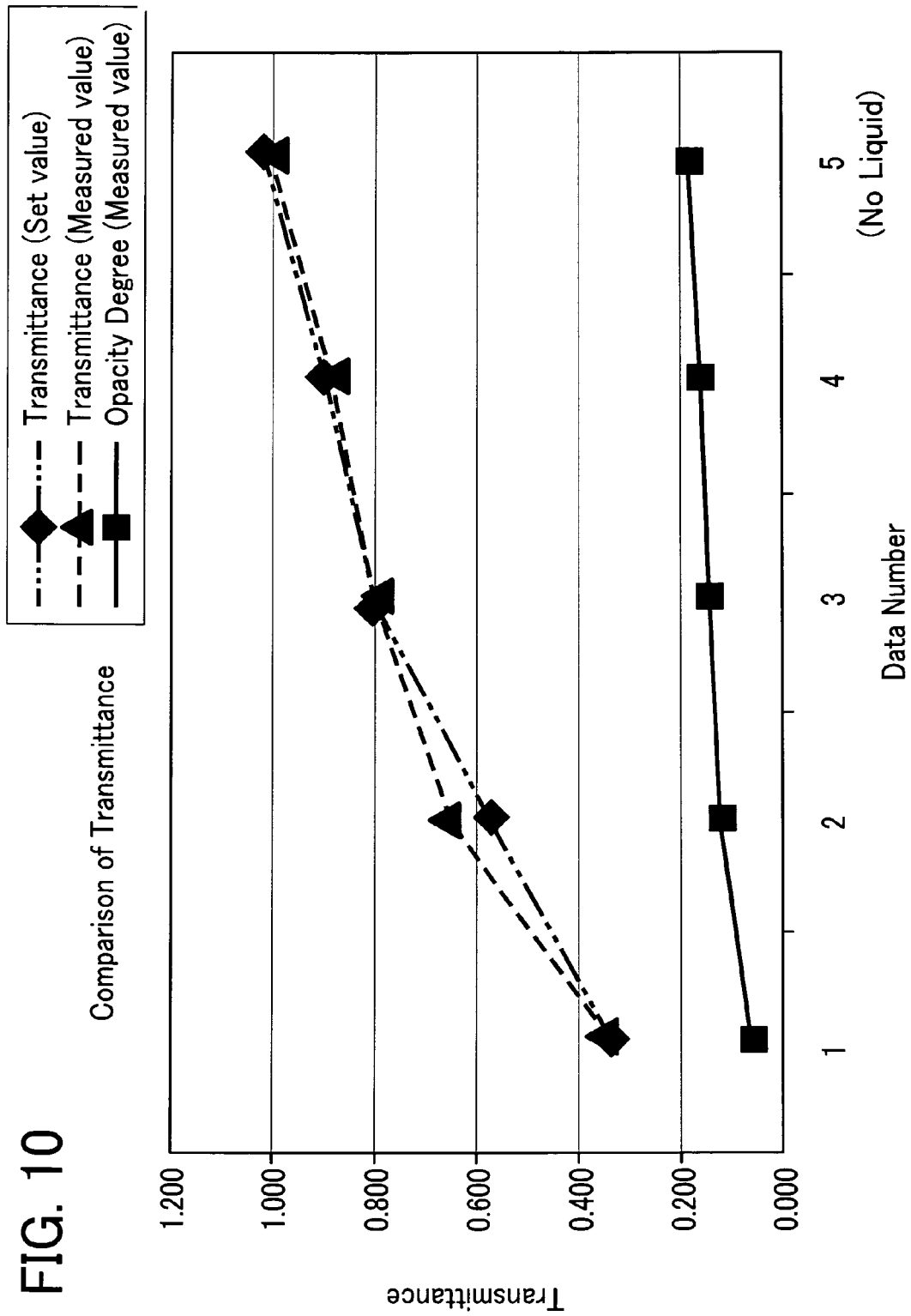

OPHTHALMIC APPARATUS, ANALYSIS PROGRAM, OPTIC MEDIA OPACITY ACQUIRING METHOD, AND FLUORESCENCE INTENSITY ACQUIRING METHOD

CROSS-REFERENCE TO RELATED APPLICATIONS

This application is based upon and claims the benefit of priority from the prior Japanese Patent Applications No. 2013-096180 filed on May 1, 2013 and No. 2013-201984 filed on Sep. 27, 2013, the entire contents of which are incorporated herein by reference.

BACKGROUND

This disclosure relates to an ophthalmic apparatus to examine an examinee's eye, an analysis program to analyze a state of the examinee's eye, a method for acquiring an degree of opacity in an optic media of the examinee's eye, and a method for acquiring fluorescence intensity.

RELATED ART

As one type of ophthalmic apparatus for examining an examinee's eye, there has conventionally been known an ophthalmic apparatus arranged to project light to each point on a fundus of the eye and cause a light receiving element to receive light emitted from each point on the fundus resulting from the projected light in order to acquire information according to the intensity of light emitted from each point on the fundus. For instance, there is an apparatus configured to project light to a fundus of an examinee's eye, causing auto-fluorescence in an auto-fluorescence material accumulated in the fundus (fundus-auto-fluorescence: FAF) to measure the intensity of auto-fluorescence in order to check the degree of accumulation of the auto-fluorescence material (e.g., lipofuscin) in the fundus (JP-A-2006-247076).

SUMMARY

Meanwhile, in case an optic media of an examinee's eye has opacity due to cataract or the like, information to be obtained by the ophthalmic apparatus may be influenced by the opacity of the optic media. This is because the light projected from the ophthalmic apparatus to the fundus and the light emitted from each point on the fundus resulting from the light projected from the ophthalmic apparatus are blocked or scattered by the opacity of the optic media. In addition, as the degree of opacity in the optic media is larger, the light is scattered or the like by the opacity at a higher ratio. In some cases, accordingly, the degree of opacity in the optic media of the eye is requested to be determined.

The present disclosure has been made in view of the above circumstances and has a purpose to provide an apparatus, a program, and a method to determine the degree of opacity occurring in an optic media of an examinee's eye.

A first aspect of the present disclosure provides an ophthalmic apparatus including: a light projecting optical system to project light to each point on a fundus of an examinee's eye; a light receiving optical system including a light receiving element to receive light from the fundus emitted from each point on the fundus resulting from the light projected from the light projecting optical system; and a controller for controlling the ophthalmic apparatus, wherein the controller is configured to: acquire intensity information representing intensity of the light from the fundus corresponding to each point on the fundus based on a result of received light of the light receiving element; and analyze a degree of opacity in an optic media of the examinee's eye based on the intensity information.

A second aspect of the present disclosure provides an analysis program to be executed in an analysis device to analyze a state of an examinee's eye by use of intensity information indicating intensity of light from a fundus of the eye resulting from light projected to each site on the fundus, wherein the program is executed by a processor of the analysis device to cause the analysis device to execute an analysis step of analyzing a degree of opacity in an optic media of the eye based on the intensity information.

A third aspect of the present disclosure provides a method for acquiring a degree of opacity in an optic media, the method including: a first intensity information acquiring step of acquiring first intensity information of light emitted from each site on a fundus of an examinee's eye by projecting first light of a first wavelength to each site on the fundus, the first intensity information being acquired based on a signal from a light receiving element that receives the light from the fundus; a second intensity information acquiring step of acquiring second intensity information of light emitted from each site on the fundus by projecting second light having a shorter wavelength than the first wavelength to each site on the fundus, the second intensity information being acquired based on a signal from the light receiving element; and an opacity acquiring step of acquiring the degree of opacity in the optic media of the examinee's eye by use of a ratio between intensity of the light from the fundus resulting from the first light indicated by the first intensity information and intensity of the light from the fundus resulting from the second light indicated by the second intensity information.

A fourth aspect of the present disclosure provides a method for acquiring fluorescence intensity, the method including: a first light projecting and receiving step of projecting light to an examinee's eye and receiving light returning from an optic media of the eye or a site closer to a fundus of the eye than the optic media through a first light receiving element; a second light projecting and receiving step of projecting excitation light to the fundus of the eye to excite a fluorescent material existing in the fundus and emit fluorescence, and receiving the light through a second light receiving element that is the same as or separate from the first light receiving element; an opacity acquiring step of acquiring a degree of opacity in the optic media of the eye based on a signal output from the first light receiving element that receives the returned light in the first light projecting and receiving step; a fluorescence intensity acquiring step of acquiring intensity of the fluorescence from the fundus of the eye based on a signal output from the second light receiving element that receives the fluorescence in the second light projecting and receiving step; and a correcting step of correcting the intensity of the fluorescence obtained in the fluorescence intensity acquiring step by use of the degree of opacity in the optic media of the eye acquired in the opacity acquiring step.

BRIEF DESCRIPTION OF THE DRAWINGS

FIG. 10 is a graph showing opacity degree and transmittance of an optic media measured by the ophthalmic apparatus.

DETAILED DESCRIPTION OF THE EXEMPLARY EMBODIMENTS

Figure 1:
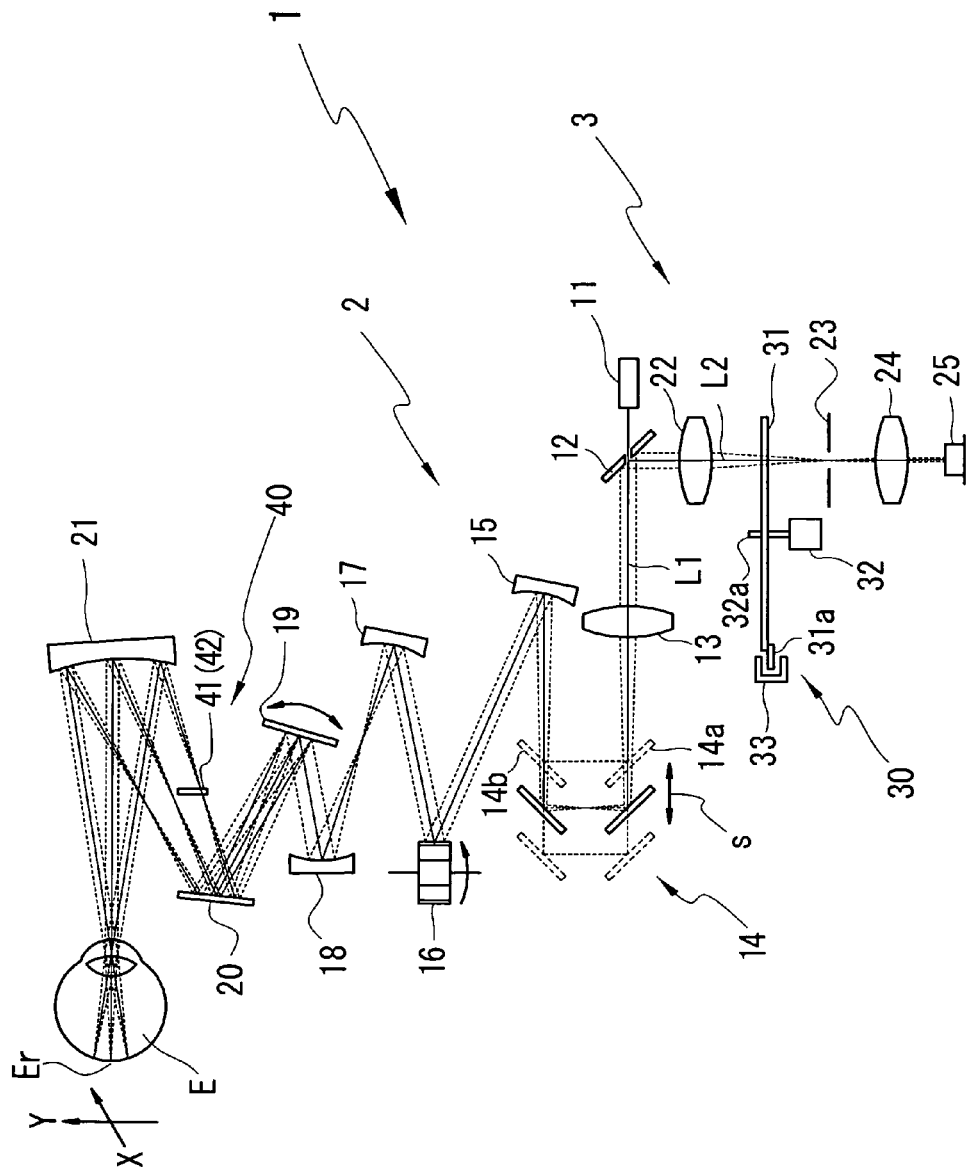
FIG. 1 is a schematic configuration diagram showing optical systems contained in an ophthalmic apparatus of an embodiment.

As one example of embodiments of this disclosure, an ophthalmic apparatus 1 will be explained below referring to accompanying drawings. Referring to FIG. 1, optical systems of the ophthalmic apparatus 1 will be first explained. The ophthalmic apparatus 1 is an ophthalmic equipment to examine an examinee's eye ("eye") E. In the present embodiment, the ophthalmic apparatus 1 is explained as a scanning laser ophthalmoscope (SLO) capable of photographing a fundus Er by each of reflected light from the fundus ("fundus reflection light") and auto-fluorescence of a material accumulated in the fundus Er.

In the present embodiment, the ophthalmic apparatus 1 includes a light projecting optical system 2, a light receiving optical system 3, a rotary disc unit 30, and a standard sample unit 40. The light projecting optical system 2 is first explained. This light projecting optical system 2 is configured to project light (illumination light and excitation light) to each point in a photographing area of the fundus Er of the eye E. In the present embodiment, the light projecting optical system 2 includes a laser beam emitting part 11, a perforated mirror 12, a lens 13, a diopter correction part 14, a concave mirror 15, a polygon mirror 16, a concave mirror 17, a concave mirror 18, a galvano mirror 19, a mirror 20, and a concave mirror 21.

Figure 2:
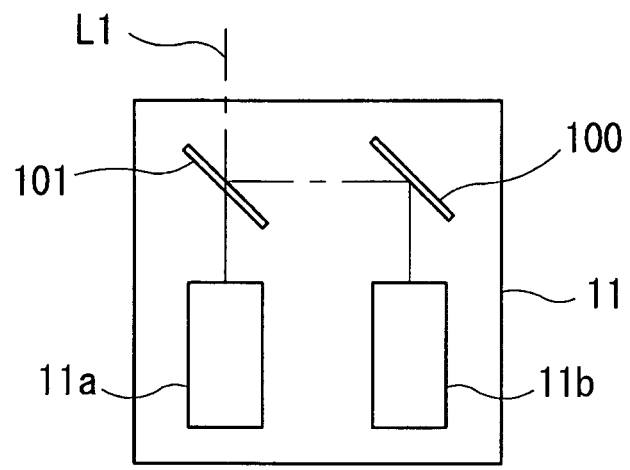
FIG. 2 is a diagram showing a detailed configuration of a laser emitting part.

The laser beam emitting part 11 is configured to emit at least a laser beam of a first wavelength and a laser beam of a second wavelength. In the present embodiment, as shown in FIG. 2, the laser beam emitting part 11 includes a first laser source 11a, a second laser source 11b, a mirror 100, and a dichroic mirror 101. In the present embodiment, the first laser source 11a emits a laser beam (first light) having a wavelength of about 790 nm in an infrared region. The second laser source 11b emits a laser beam (second light) having a wavelength of about 490 nm in a visible region. The infrared laser beam emitted from the first laser source 11a passes through the dichroic mirror 101, goes out of the laser beam emitting part 11 and travels along an optical axis L1. The visible laser beam emitted from the second laser source 11b is deflected by the mirror 100 and then reflected by the dichroic mirror 101 to travel along the optical axis L1. In the present embodiment, the two laser sources 11a and 11b may be turned on simultaneously or only one of them may be turned on.

The laser beam emitted from the laser beam emitting part 11 passes through an opening formed at the center of the perforated mirror 12, and passes through the lens 13, and then is reflected by the diopter correction part 14 and the concave mirror 15, thereby traveling toward the polygon mirror 16.

The light reflected by the polygon mirror 16 is reflected by the concave mirrors 17, 18, galvano mirror 19, mirror 20, concave mirror 21, and then comes into focus on the fundus Er of the eye E.

The diopter correction part 14 is a mechanism to correct diopter. This diopter correction part 14 includes two mirrors 14a and 14b and a drive part not shown. The drive part moves the two mirrors 14a and 14b in a direction indicated by an arrow s while keeping the positional relationship between the two mirrors 14a and 14b. This changes an optical path length of the light projecting optical system 2 and an optical path length of the light receiving optical system 3 mentioned later, thereby performing diopter correction of the ophthalmic apparatus 1.

The polygon mirror 16 is rotated by a motor not shown to move an irradiation position (a scanning point) of a laser beam on the fundus Er in a horizontal direction (i.e., an X direction) of the fundus Er. When the polygon mirror 16 is rotated while the laser beam is being emitted from the laser beam emitting part 11, accordingly, the laser beam is scanned in the horizontal direction on the fundus.

Further, the galvano mirror 19 is rotated (swung) by a motor not shown to move the irradiation position of the laser beam on the fundus Er in a vertical direction (i.e., a Y direction) on the fundus. When the galvano mirror 19 is rotated while the laser beam is being emitted from the laser beam emitting part 11, accordingly, the laser beam is scanned in the vertical direction on the fundus. In this way, the polygon mirror 16 and the galvano mirror 19 are driven to two-dimensionally scan the fundus Er with the laser beam.

In association with irradiation of the laser beam from the laser beam emitting part 11 to the fundus Er, light is emitted from the fundus Er. To be concrete, part of the laser beam is reflected by the fundus Er. Accordingly, the light reflected by the fundus Er emerges from a pupil. Furthermore, part of the laser beam excites an auto-fluorescence material existing in the fundus Er. In the present embodiment, it is conceived that part of the laser beam of the second wavelength excites lipofuscin accumulated in the fundus Er. Accordingly, fluorescence emitted from the auto-fluorescence material of the fundus Er also emerges from the pupil. In general, fluorescence emitted from an auto-fluorescence material is dimmer than fundus reflection light. When an examinee's eye E is to be photographed with the fundus reflection light, therefore, the auto-fluorescence produced in the fundus Er is considered to be less likely to cause a problem.

The photographing optical system 3 is explained below. This photographing optical system 3 is a light receiving optical system to receive the light from the fundus Er resulting from the laser beam from the light projecting optical system 2 (that is, the fundus reflection light during normal photographing and the fluorescence produced in the fundus Er during fluorescence photographing). In the present embodiment, the photographing optical system 3 shares each component placed on the optical path L1 of the light projecting optical system 2, i.e., from the perforated mirror 12 to the concave mirror 21, with the light projecting optical system 2. The photographing optical system 3 in the present embodiment further includes a lens 22, a pinhole plate 23, a lens 24, and a light receiving element 25.

When the laser beam is to be irradiated to the fundus of the eye E, the light reflected or emitted from the fundus Er resulting from the laser beam reversely travels along the aforementioned light projecting optical system 2, is reflected by the perforated mirror 12, and thus delivered to the lens 22. The pupil position of the eye E and the opening of the perforated mirror 12 are placed in an optically conjugate relation. The light delivered to the lens 22 from the fundus Er comes into focus on a pinhole of the pinhole plate 23. The focused light from the fundus Er is received by the light receiving element 25 through the lens 24. The light receiving element 25 used in the present embodiment is an APD (avalanche photodiode) having sensitivity to light of wavelengths in a visible region and an infrared region.

The rotary disc unit 30 selectively allows a wavelength of light to be received by the light receiving element 25. This rotary disc unit 30 includes a rotary disc 31, a pulse motor 32, and a sensor 33.

The rotary disc 31 is a disc provided with a barrier filter to observe fluorescence produced in the fundus Er. The rotary disc 31 is placed so that an optical axis L2 passes through a part of a plate surface apart from the center of the rotary disc 31 and the plate surface of the rotary disc 31 is perpendicular to the optical axis L2. The pulse motor 32 is a device to rotate the rotary disc 31 through a rotary shaft 32a fixed at the center of the rotary disc 31. The sensor 33 is a detection device to detect the position of the rotary disc 31 (rotation angle detection). When a shielding plate 31a provided in a predetermined position of the rotary disc 31 overlaps with the sensor 33, a reference position of the rotary disc 31 is detected. In the present embodiment, with reference to the reference position, the rotation angle of the rotary disc 31 is adjusted.

Figure 3:
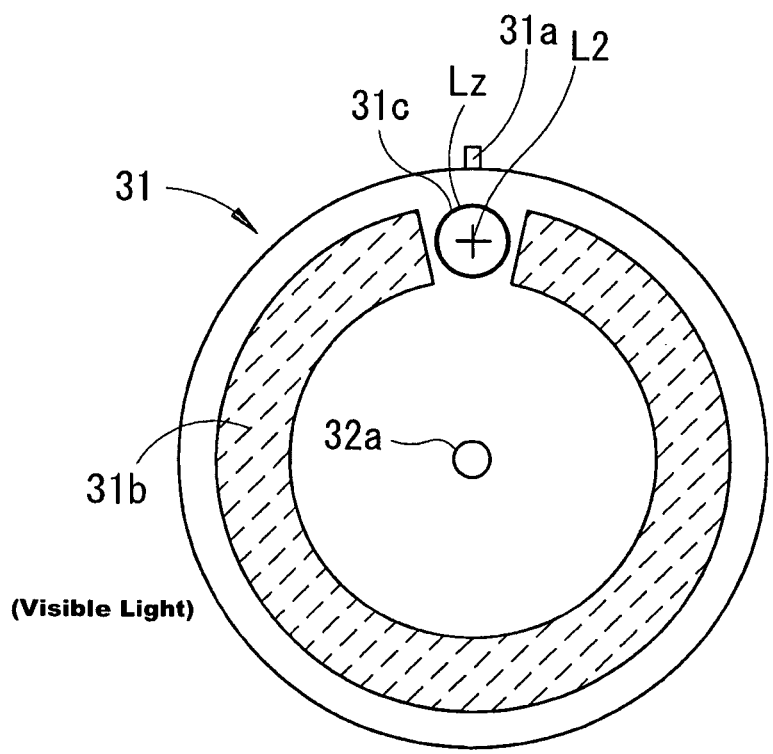
FIG. 3 is a diagram showing a detailed configuration of a rotary disc.

Herein, referring to FIG. 3, the configuration of the rotary disc 31 will be explained in detail. FIG. 3 shows the rotary disc 31 seen from the side of the lens 22. L2 indicates a photographing optical axis of the photographing optical system 3 and Lz indicates a photographing region of the photographing optical system 3.

The rotary disc 31 is provided with a filter 31b. This filter 31b is a barrier filter used for photographing visible fluorescence. The filter 31b has a spectral property shown in FIG. 4. In the present embodiment, the filter 31b is used for FAF (fundus-auto-fluorescence) photographing conducted by irradiating a laser beam of a second wavelength (a laser beam in a visible region) to a fundus. The FAF photographing in the present embodiment is fluorescence photographing utilizing the principle that lipofuscin of a retinal pigment epithelium exhibits auto-fluorescence (a wavelength of about 500 nm to a wavelength of about 750 nm) by the second laser source 11b (a wavelength of about 490 nm).

Figure 4:
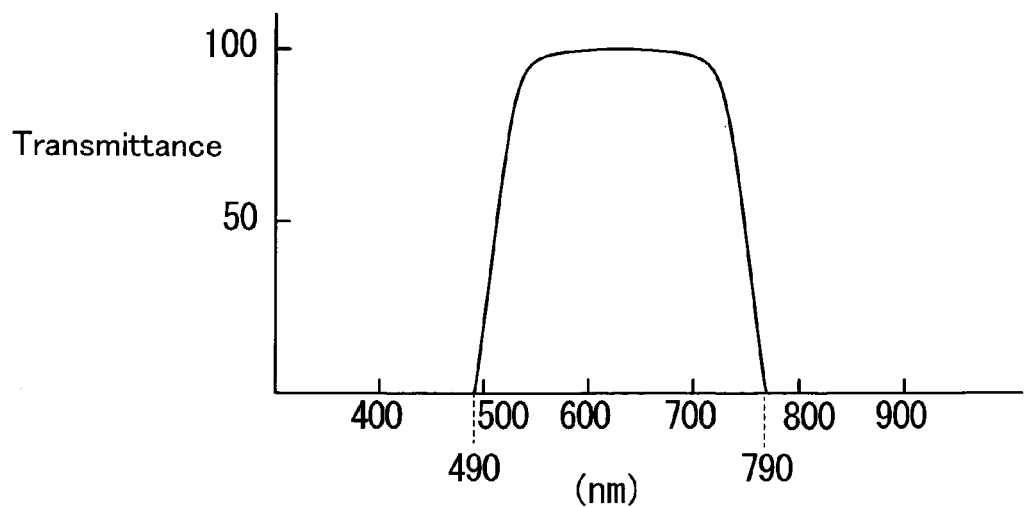
FIG. 4 is a graph showing a filtering property of a filter of the rotary disc.

In the present embodiment, as shown in FIG. 4, the filter 31b allows transmission of fluorescence produced in the fundus Er by the laser beam emitted from the second laser source 11b as excitation light. On the other hand, the filter 31b blocks or intercepts the laser beam in an infrared region emitted from the first laser source 11a, the laser beam in a visible region emitted from the second laser source 11b, and the fluorescence produced in the fundus by the laser beam emitted from the first laser source 11a as the excitation light.

Although the present embodiment describes the FAF photographing to be performed based on light emission of lipofuscin, the photographing may also be conducted by light emission of other auto-fluorescence materials existing in the fundus Er and a fluorescence contrast agent or the like dispensed to the fundus. In this case, a light source and a filter have only to be provided in accordance with the fluorescence characteristic of a fluorescence material targeted for light emission.

The filter 31b is, as shown in FIG. 3, placed on the path or trajectory of the photographing region Lz which will pass through the filter 31b while the rotary disc 31 is rotated.

Furthermore, an opening 31c is provided in the rotary disc 31 on the trajectory of the passage region of the photographing region Lz. The opening 31c is disposed on the optical axis L2 during positional alignment between the eye E and the apparatus and during normal observation of the fundus. At that time, the opening 31c allows all light beams from the fundus Er to pass through to reach the light receiving element 25. The size of the opening 31c in the present embodiment is designed to be nearly equal to the size of the photographing region Lz of the photographing optical system 3.

As shown in FIG. 1, the standard sample unit 40 is provided on a common optical path of the light projecting optical system 2 and the photographing optical system 3. To be concrete, the standard sample unit 40 is provided between the concave mirror 21 and the mirror 20. In the present embodiment, even though the details will be mentioned later, the standard sample unit 40 is a unit to be photographed together with the fundus Er to make the ophthalmic apparatus 1 acquire the reference used to determine various kinds of information such as the fluorescence intensity of auto-fluorescence and the degree of opacity in the optic media.

Figure 5:
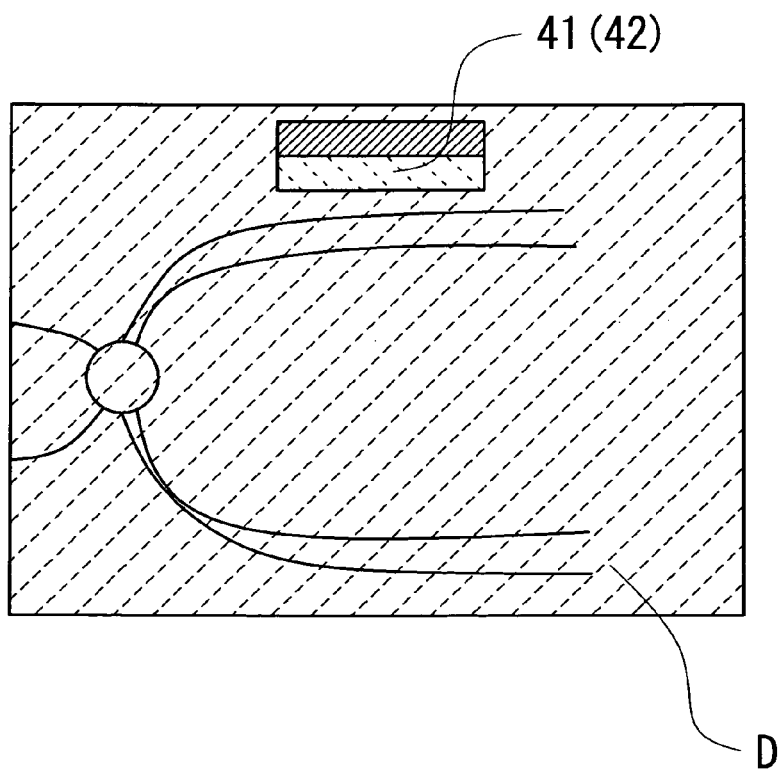
FIG. 5 is a schematic diagram schematically showing a fundus image photographed by the ophthalmic apparatus.

The standard sample unit 40 includes a reflection standard sample 41 (a first reference part 41) and a fluorescence standard sample 42 (a second reference part 42). In the present embodiment, either one of the reflection standard sample 41 and the fluorescence standard sample 42 is placed between the concave mirror 21 and the mirror 20 and within a passage region of a laser beam (that is, within a scanning range, within a photographing range) when the laser beam scans the fundus Er of the eye E. When the laser beam is irradiated, the standard sample 41 or 42 placed within the light passage region emits (reflects or irradiates) reference light (reflection light or fluorescence). The reference light emitted by the standard sample 41 or 42 reversely travels along the light projecting optical system 2 and passes through the lens 22, and then reaches the light receiving element 25 of the light receiving optical system 3. Thus, the standard sample 41 is photographed together with the fundus Er as shown in FIG. 5.

The standard samples 41 and 42 is arranged in the vicinity of the outer edge of the passage region of the laser beam. Accordingly, the information of a noticeable site (e.g., image center) of a fundus image obtained during photographing is not largely diminished by the standard sample 41, 42.

One of the standard samples 41 and 42 placed within the passage region of the laser beam becomes conjugated with the fundus Er when diopter correction is performed with respect to the eye E of 0 diopter. The reflection standard sample 41 and the fluorescence standard sample 42 are changed from one to the other by a drive mechanism not shown so that one of the standard samples 41 and 42 is inserted in the laser beam passage region.

Figure 6:
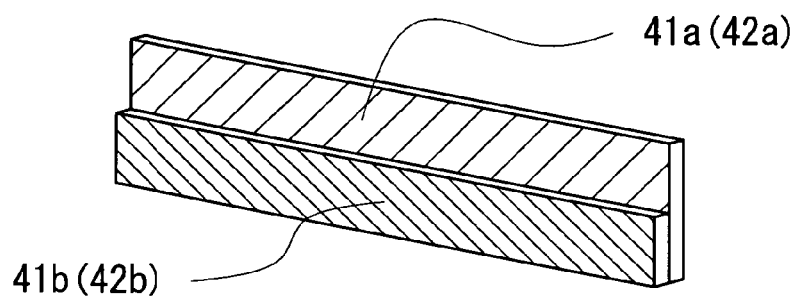
FIG. 6 is a detailed configuration view of a standard sample.

The reflection standard sample 41 is a member to be photographed to normalize the intensity of the fundus reflection light received by the light receiving element 25. As shown in FIG. 6, this reflection standard sample 41 is provided with a white member 41a and a black member 41b. The white member 41a is a member that diffusely reflects most part of a laser beam irradiated thereto. As the white member 41a, for example, a white paper and a component applied with barium sulfate may be used. As the black member 41b, any member may be used as long as it absorbs most part of a laser beam irradiated thereto. For example, a black flocked sheet and a member applied with matte-black coating.

The fluorescence standard sample 42 is a member to be photographed to calculate the intensity of fluorescence emitted from the fundus of the eye E. The fluorescence standard sample 42 is provided with a fluorescence member 42a and a black member 42b. In the present embodiment, the fluorescence member 42a is a member that emits fluorescence by predetermined excitation light (a laser beam in a visible region emitted from the second laser source). The fluorescence member 42a is a fluorescence material having a property of producing fluorescence by the wavelength of the excitation light used herein. For instance, when fluorescence is to be obtained under the condition that the visible laser beam from the second laser source 11b is excitation light and the filter 31b is a barrier filter, FLUOR-REF Red by MICROSCOPY/MICROSCOPY EDUCATION may be used. As the black member 42b, any member that does not generate fluorescence even when it is irradiated with excitation light may be selected.

In the present embodiment, one of the standard samples 41 and 42 disposed in the photographing range is located in a position conjugate with the fundus Er of the eye E when the eye E of 0 diopter is subjected to diopter correction. However, the placement of the standard sample 41, 42 is not limited to the above as long as the standard sample 41, 42 is positioned within the scanning range of a laser beam.

Figure 7:
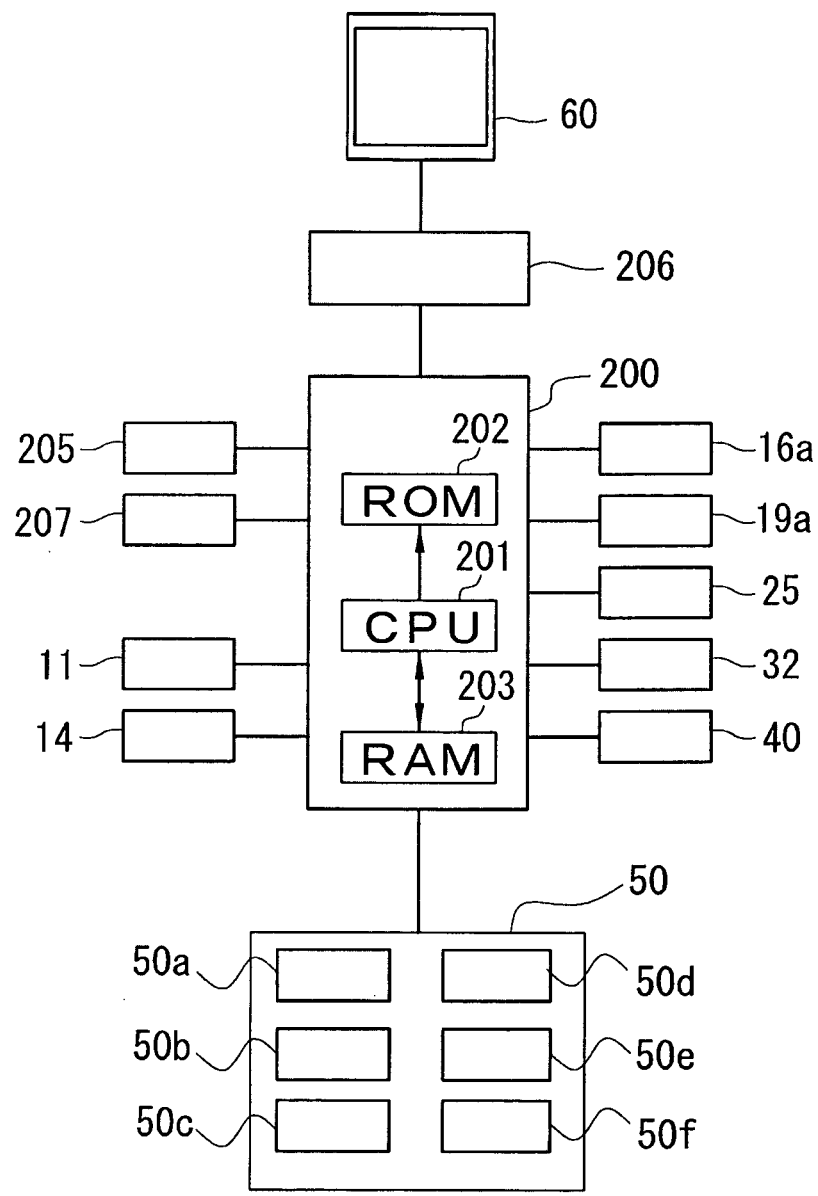
FIG. 7 is a schematic configuration view showing a control system of the ophthalmic apparatus.

FIG. 7 is a block diagram showing a control system of the ophthalmic apparatus 1 in the present embodiment. Main control of the ophthalmic apparatus 1 is executed by a control part 200. This control part 200 is a processing device having an electronic circuit to perform control processing of each part of the ophthalmic apparatus 1 and arithmetic processing of measurement results.

In the present embodiment, the control part 200 is connected to a flash memory 205, an image processing IC 206, a lens transmittance database 207, the laser beam emitting part 11, the diopter correction part 14, a motor 16a for driving the polygon mirror, a motor 19a for driving the galvano mirror, the light receiving element 25, the pulse motor 32, the standard sample unit 40, and an operation part 50. The control part 200 is also connected to a monitor 60 through the image processing IC 206. The monitor 60 is a display device for displaying an image of the eye E photographed by the ophthalmic apparatus 1 and various measurement results.

The control part 200 includes a CPU 201, a ROM 202, and a RAM 203. The CPU 201 is a processing device to execute various processings for the ophthalmic apparatus 1. The ROM 202 is a nonvolatile storage device storing a control program and fixed data. The RAM 203 is a rewritable volatile storage device. The RAM 203 stores for example temporary data to be used by the ophthalmic apparatus 1 at the time of photographing and measuring the eye E.

The flash memory 205 is a rewritable nonvolatile storage device. The flash memory 205 stores at least a program to cause the control part 200 to execute a fluorescence-image photographing and analyzing processing which will be mentioned later.

The image processing IC 206 is a processing device to create a fundus image of the eye E based on a signal received by the light receiving element 25. The image processing IC 206 constructs (generates) image data of the fundus image corresponding to one frame based on the received signals sequentially output from the light receiving element 25, and outputs the image data to the monitor 60.

The lens transmittance database 207 is a database that stores lens transmittances previously measured on a plurality of eyes of examinees. In the present embodiment, even though the details will be mentioned later, the lens transmittances in the lens transmittance database 207 are values determined by use of fundus images of each examinee's eye having been subjected to a cataract operation (e.g., IOL operation) and photographed before and after the operation.

The operation part 50 is provided with an input device such as switches to be operated by an examiner. In the present embodiment, there are provided various switches including a mode changeover switch 50a, a light source selection switch 50b, a light amount adjustment dial 50c, a refractive value input switch 50d, a joystick 50e, and a photograph switch 50f.

The mode changeover switch 50a is a switch to change over the ophthalmic apparatus 1 to be controlled by the control part 200 between a manual photographing mode and a FAF photographing mode. The manual mode, the details of which will be explained later, is a mode to observe a fundus with a fundus reflection light resulting from the infrared light. The FAF photographing mode is a mode to observe autofluorescence produced in the fundus Er. The light source selection switch 50b is a switch to select a wavelength of a laser beam to be emitted from the laser beam emitting part 11. An examiner operates the light source selection switch 50b to select a light source to be turned on and off, from the first laser source 11a and the second laser source 11b. The light amount adjustment dial 50c is a dial to change the light amount of a laser beam to be emitted from the laser beam emitting part 11.

In the present embodiment, the light amount adjustment dial 50c includes two dials; a light amount adjustment dial for the first laser source 11a and a light adjustment dial for the second laser source 11b. The refractive value input switch 50d is a switch to allow an examiner to input a previously measured refractive value of the eye E. The joystick 50e is an input device to be operated by an examiner to designate a photographing range of the fundus Er. The control part 200 drives a drive mechanism not shown in response to operation of the joystick 50e to move the ophthalmic apparatus 1 with respect to the eye E. The photographing switch 50f is a switch to be operated to photograph (capture) a fundus image.

Operations of the ophthalmic apparatus configured as above will be explained below. Herein, the following explanation is given to a method for performing positional alignment of the ophthalmic apparatus 1 with respect to the eye E in the manual photographing mode, conducting photographing in the FAF photographing mode (FAF photographing), and analyzing the auto-fluorescence image.

<Manual Photographing Mode>

An examiner first manipulates the mode changeover switch 50a to select the manual photographing mode in order to make positional alignment of the ophthalmic apparatus 1 with respect to the eye E. The control part 200 thus drives the pulse motor 32 to adjust the rotation angle of the rotary disc 31 so as to align the opening 31c of the rotary disc 31 with the optical axis L2. The control part 200 further drives the drive mechanism (not shown) of the standard sample unit 40 to set the reflection standard sample 41 onto the optical path L1.

The examiner then operates the light source selection switch 50b to select a state of turning on only the first laser source 11a. Accordingly, the control part 200 turns on the first laser source 11a. Furthermore, the examiner inputs the previously measured refractive value of the eye E with the refractive value input switch 50d. The control part 200 drives the drive mechanism not shown of the diopter correction part 14 to move the mirrors 14a and 14b to respective positions according to the refractive value. In this manner, the diopter correction is performed.

Furthermore, the examiner operates the joystick 50e to change the photographing position of the ophthalmic apparatus 1 with respect to the eye E. The control part 200 drives the drive mechanism not shown in response to an operation signal output from the joystick 50e to move the optical systems of the ophthalmic apparatus 1 with respect to the eye E. Herein, the examiner makes alignment of the ophthalmic apparatus 1 with the eye E so that a desired site on the fundus is irradiated by the laser beam and displayed on the monitor 60.

The control part 200 further drives the polygon mirror 16 and the galvano mirror 19 to scan the laser beam on the fundus of the eye E in two dimensions. Accordingly, the fundus reflection light corresponding to the scan position of the laser beam on the fundus is sequentially received by the light receiving element 25. The reflection standard sample 41 is placed in the scanning region of the laser beam. In a case where the laser beam is irradiated to the reflection standard sample 41, therefore, the reflection light from the reflection standard sample 41 is received by the light receiving element 25. As the reflection light from the fundus Er or the reflection standard sample 41 is received by the light receiving element 25, received light signals from the light receiving element 25 are sequentially transmitted to the image processing IC 206.

The image processing IC 206 constructs image data of a single fundus image (an image corresponding to one frame) in a state including the reflection information from the reflection standard sample 41 based on the received signals from the light receiving element 25, and outputs the image data to the monitor 60. The above generation and output of the fundus image are repeated every scanning of one frame by the polygonal mirror 16 and the galvano mirror 19, so that the fundus of the eye E can be observed in the form of a moving image in real time on a screen of the monitor 60.

Under the above control, the monitor 60 displays the fundus image photographed with the infrared light as a moving image. The examiner operates the operation part 50 to bring the fundus image into focus while watching the fundus image displayed on the monitor 60. When it is confirmed that the eye E and the ophthalmic apparatus 1 are in proper positional relation, the examiner operates the mode changeover switch 50a to select the FAF photographing mode.

<FAF Photographing Mode>

When the FAF photographing mode is selected, the control part 200 executes the following control while maintaining the operations of the polygon mirror 16 and the galvano mirror 19. Specifically, the control part 200 stops emission of the infrared light from the first laser source 11a and also rotates the rotary disc 31 to bring the filter 31b onto the optical axis L2. Further, the control part 200 sets the fluorescence standard sample 42 onto the optical path.

Subsequently, the control part 200 causes the second laser source 11b to emit a visible laser beam. As described above, the visible laser beam output from the second laser source 11b excites lipofuscin accumulated in the fundus, generating fluorescence (auto-fluorescence). The filter 31b transmits fluorescence emitted from lipofuscin and blocks the fundus reflection light of the second laser source 11b. Accordingly, the light receiving element 25 receives the fluorescence produced in the fundus. Thus, the fluorescence (auto-fluorescence image) produced in the fundus of the eye E is displayed as a moving image on the monitor 60. This enables the examiner to observe the fluorescence produced in the fundus of the eye E through the monitor 60. The examiner operates the light amount adjustment dial 50c to adjust the brightness of the auto-fluorescence image to make this image easily viewable. Accordingly, the control part 200 changes the light amount output from the second laser source 11b to the light amount indicated by the dial 50c.

When an appropriate auto-fluorescence image (a moving image) comes to be observable, the examiner operates the photographing switch 50f. When this switch 50f is operated, the control part 200 executes the fluorescence image photographing and analyzing processing. This fluorescence image photographing and analyzing processing includes photographing a still image of the auto-fluorescence image and determining the intensity of the auto-fluorescence in a photographed area of the auto-fluorescence image.

Figure 8:
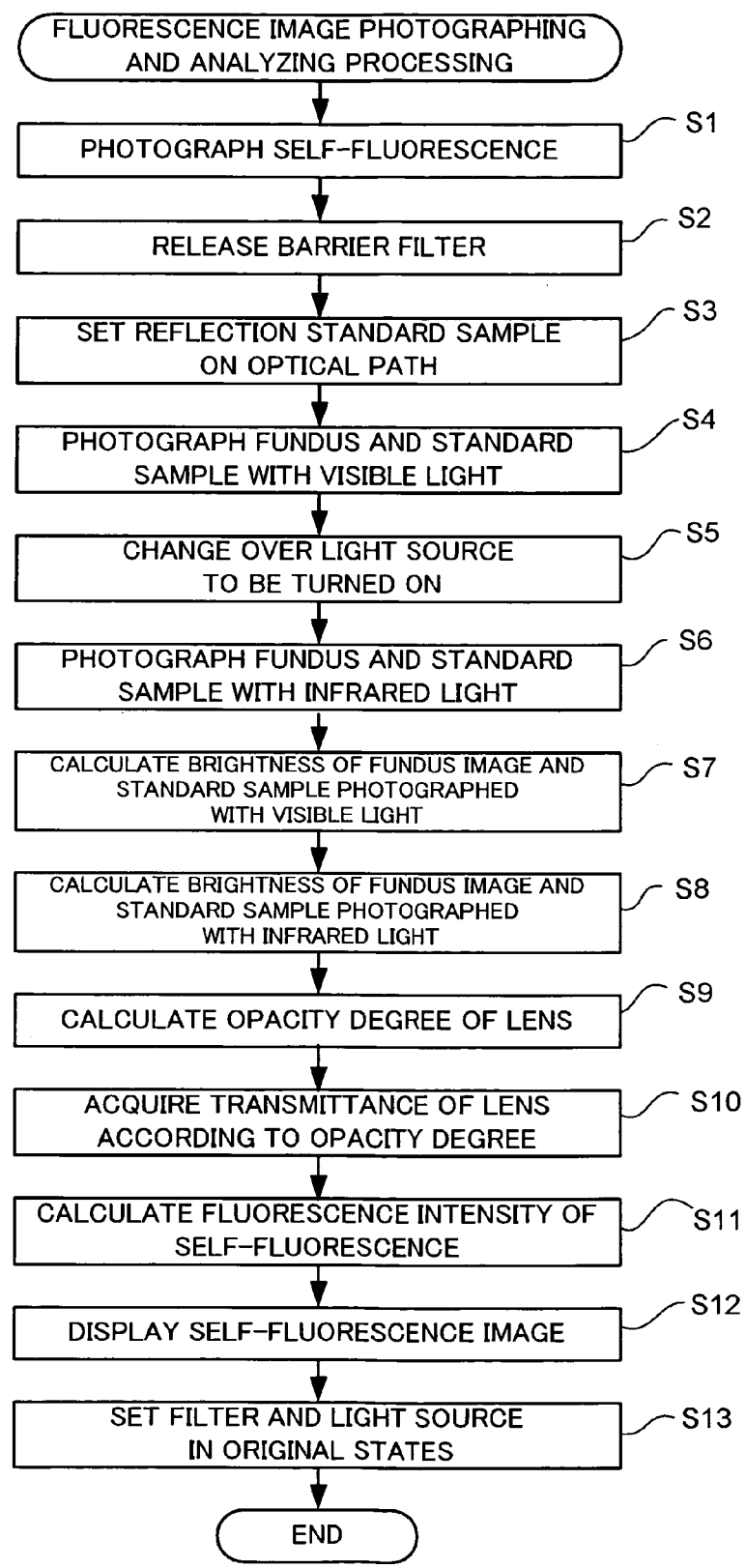
FIG. 8 is a flowchart showing fluorescence image analyzing processing to be executed by a CPU.

The fluorescence image photographing and analyzing processing will be explained below referring to FIG. 8. A processing of photographing the still image of the auto-fluorescence image is first executed (S1). The CPU 201 drives the polygon mirror 16 and the galvano mirror 19 and stores, in the RAM 203, the image data of one auto-fluorescence image created by the image processing IC 206 in conjunction with scanning by the polygon mirror 16 and the galvano mirror 19. The image data includes a two-dimensional coordinate and gradation information (gradation value) of each pixel. In the present embodiment, a relationship (gradation characteristic) between a signal intensity of the received light signal output from the light receiving element 25 to the image processing IC 206 and the gradation value of each pixel is represented by linear characteristics. A relationship (gradation characteristic) between the intensity of light emitted from the fundus (received light intensity) and received by the light receiving element 25 and the gradation value of each pixel is also represented by linear characteristics. In the present embodiment, accordingly, the control part 200 acquires the intensity of reflection light reflected by each point on the fundus Er (one example of the light from the fundus), that is, the intensity of light received by the light receiving element 25, as the image data output from the image processing IC 206.

As mentioned above, the fluorescence standard sample 42 is placed in the scanning range of the laser beam. Therefore, as shown in FIG. 5, the captured image includes a fundus image portion D obtained by fluorescence photographing and an image of the fluorescence standard sample 42 photographed together.

In the present embodiment, the image data of the auto-fluorescence image corresponding to one frame is stored in the RAM 203. In general, as described above, the intensity of auto-fluorescence is weak and thus an image obtained by addition processing of the fundus images corresponding to a plurality of frames may be stored in the RAM 203.

Successively, the CPU 201 executes the processing in S2 and subsequent steps to derive the fluorescence intensity of auto-fluorescence in the photographing range of the auto-fluorescence image (still image). In the processing in S2, the CPU 201 rotates the rotary disc 31 to move the filter 31b away from the optical axis L2 and dispose the opening 31c on the optical axis L2 (S2). Accordingly, the light receiving element 25 receives not only the fluorescence produced in the fundus but also the fundus reflection light resulting from the visible laser beam emitted from the second light source 11b. The CPU 201 drives the drive mechanism (not shown) of the standard sample unit 40 to retract the fluorescence standard sample 42 from the optical path and instead insert the reflection standard sample 41 to the optical path (S3).

The CPU 201 then photographs the fundus image (still image) based on the visible fundus reflection light and stores the image data of the fundus image in the RAM 203 (S4). In the present embodiment, the processing in S4 is similar to that in S1 and thus is not explained in detail herein. Since the reflection standard sample 41 is placed on the optical path in the laser beam scanning range, the photographed fundus image includes the fundus image portion D and a reflection image from the reflection standard sample 41 (see FIG. 5).

The CPU 201 changes over the laser beam to be turned on (S5). To be concrete, the CPU 201 turns off the second laser source 11b and turns on the first laser source 11a. Thus, the examinee's eye E is irradiated by the infrared laser beam. Similar to each processing in S1 and S4, the CPU 201 photographs the fundus image (still image) based on the fundus reflection light resulting from the infrared laser beam and stores the image data of the fundus image in the RAM 203 (S6). The image photographed with the infrared light includes the fundus image portion D and the reflection image from the reflection standard sample 41.

Subsequently, referring to the image data stored in the RAM 203 in the processing in S4, the brightness Bb of the fundus image is calculated based on the fundus reflection light resulting from the visible laser beam (S7). Bb is given by the following expression (1):

$$Bb = \frac{Lb - Vb}{Ub - Vb} \quad (1)$$

where Lb denotes an average gradation value in the region except the reflection standard sample 41 (i.e., the fundus image portion D) in the image photographed with the fundus reflection light of the visible laser beam, Ub is an average gradation value in a portion corresponding to the white member 41*a* of the reflection standard sample 41, and Vb is an average gradation value in a portion corresponding to the black member 41*b* of the reflection standard sample 41. A gradation value of a background is indicated by the average gradation value Vb. Thus, (Lb-Vb) indicates a substantial gradation value of the fundus image portion D and (Ub-Vb) indicates a substantial gradation value of the portion corresponding to the white member 41*a*. Accordingly, in the above expression (1), the substantial gradation value (Lb-Vb) of the fundus image portion is normalized (divided in the present embodiment) by the substantial gradation value (Ub-Vb) of the portion corresponding to the white member 41*a* to derive the brightness Bb.

In the present embodiment, as above, the brightness of the fundus image is determined from the average gradation value in each region (the fundus image portion D and the portion corresponding to the standard sample 41 or 42) included in the photographed image. However, the brightness of the fundus image may be determined by any other methods. For example, the brightness of the fundus image may be determined based on a central value in a gradation distribution of each region, a maximum gradation value in the gradation distribution of each region, or others. As another alternative, the brightness of the fundus image may be determined from a gradation value of a specific pixel determined in advance in each region.

Herein, the following explanation is given to that the brightness Bb is a value unlikely to be influenced by the photographing conditions of the ophthalmic apparatus 1 (properties of the apparatus). It is known that the signal intensity of the received light signal output from the light receiving element 25 varies according to the photographing conditions (properties of the apparatus) such as the light amount of a laser beam emitted from the laser beam emitting part 11 and the light receiving characteristics (gain characteristics) of the light receiving element 25. The gradation value of the fundus image is linearly related to the signal intensity of the received light signal from the light receiving element 25 and thus also varies according to the photographing conditions such as the light amount of the laser beam.

However, it is conceived that the photographing conditions such as the light amount of the laser beam have influences at equal rate on the substantial gradation value (Lb-Vb) of the fundus image portion D and the substantial gradation value (Ub-Vb) of the portion for the white member 41*a*, respectively. On the other hand, it is conceived that the ratio between the substantial gradation value (Lb-Vb) of the fundus image portion D and the substantial gradation value (Ub-Vb) of the portion for the white member 41*a* is, after all, equal to the ratio between a reflectance of the visible laser beam in the range corresponding to the fundus image portion D and a reflectance of the visible laser beam in the range corresponding to the portion for the white member 41*a*. Accordingly, in the above expression (1), the brightness Bb is considered to indicate the ratio between the reflectance of the visible laser beam in the range corresponding to the fundus image portion D and the reflectance of the visible laser beam in the range corresponding to the portion for the white member 41*a*.

Herein, it is considered that the reflectance of the visible laser beam in the range corresponding to the fundus image portion D and the reflectance of the visible laser beam in the range corresponding to the portion for the white member 41*a* are respectively values not depending on the photographing conditions such as the light amount of the laser beam. Furthermore, the reflectance (reflectance property) of the visible laser beam by the white member 41*a* is constant in every photographing irrespective of the photographing conditions such as the light amount of the laser beam. Accordingly, the ratio (brightness) Bb between the reflectance of the visible laser beam in the range corresponding to the fundus image portion D and the reflectance of the visible laser beam in the white member 41*a* is considered to be a value by which the brightness of the fundus image is estimated based on a fixed reference not depending on the photographing conditions of the ophthalmic apparatus 1. Thus, Bb is less likely to include an error resulting from the influence of the photographing conditions of the ophthalmic apparatus 1.

The ratio between the reflectance of the visible laser beam in the range corresponding to the fundus image portion D and the reflectance of the visible laser beam in the white member 41*a* is an equivalent term to the ratio between the intensity of light reflected from the white member 41*a* and received by the light receiving element 25 and the intensity of the fundus reflection light received by the light receiving element 25. Thus, the brightness Bb can be restated as a value obtained by normalizing the intensity of the fundus reflection light resulting from the visible laser beam by the intensity of the light resulting from the visible laser beam reflected from the white member 41*a*.

The CPU 201 then calculates brightness Bir of the image photographed with the infrared laser beam (S8) in a similar manner to the processing in S7. The brightness Bir is given by the following expression (2):

$$Bir = \frac{Lir - Vir}{Uir - Vir} \quad (2)$$

where Lir is an average value of gradation values of the pixels in the region of the fundus image portion D in the image photographed with the fundus reflection light resulting from the infrared laser beam, Uir is an average value of gradation values of the pixels in the image region of the white member 41*a* of the reflection standard sample 41, and Vir is an average value of gradation values of the pixels in the image region of the black member 41*b*. It is to be noted that the gradation value in each region is determined from the image data stored in the RAM 203 in the processing in S6. In the expression (2), similarly to the expression (1), the brightness Bir can be restated as a value obtained by normalizing the intensity of the fundus reflection light resulting from the infrared laser beam by the intensity of the light from the white member 41a resulting from the infrared laser beam.

The CPU 201 then determines an opacity degree P of a crystalline lens from the ratio between Bb and Bir determined in S7 and S8 as shown in the following expression (3) (S9). The opacity degree P is a parameter indicating the opacity of the optic media (the crystalline lens in the present embodiment) and tends to decrease as the opacity is higher.

$$P = \frac{Bb}{Bir} \quad (3)$$

Herein, the explanation is given to that the opacity degree P represents the degree of opacity in the optic media. In a case where the fundus image is to be photographed as in the present embodiment, as the opacity of the eye E is stronger (larger), more light is scattered. The brightness of the image is thus conceived to decrease as the opacity is stronger. It is generally known that the light of a shorter wavelength is more likely to be scattered by opacity.

Therefore, the brightness Bb and Bir of the fundus images respectively photographed with the visible light and the infrared light can be restated by the following expressions (4) and (5) respectively:

$$Bb = Rb \times (1 - Kx) \quad (4)$$

$$Bir = Rir \times (1 - x) \quad (5)$$

where x indicates the scattered light amount based on the infrared light (especially, a wavelength of a laser beam emitted from the first laser source 11b in the present embodiment). The scattered light amount in this embodiment represents the percentage of scattered light with respect to the light amount of infrared light entering in the examinee's eye E. x is a larger value as the opacity in the optic media is stronger. K is a constant larger than 1 and a value representing the extent to which the visible light is more likely to be scattered as compared with the infrared light. Further, Rb is a reflectance of the visible light and Rir is a reflectance of the infrared light.

The ratio between Bb and Bir calculated from the expressions (4) and (5) is expressed by the following expression (6):

$$\frac{Bb}{Bir} = \left\{ \frac{Rb}{Rir} \right\} \times \left\{ \frac{1 - Kx}{1 - x} \right\} \quad (6)$$

$$= \left\{ \frac{Rb}{Rir} \right\} \times \left\{ K - \frac{K - 1}{1 - x} \right\}$$

where Rb and Rir are values varying among examinees' eyes E according to individual differences such as a retinal shape. However, the ratio between Rb and Rir is conceived to be constant according to combinations of wavelengths of light to be projected irrespective of differences in eye E. Accordingly, a value of Rb/Rir can be substituted by a predetermined constant J.

Therefore, the expression (6) is rewritten as the following expression (7).

$$P = J \times \left\{ K - \frac{K - 1}{1 - x} \right\}, P = \frac{Bb}{Bir} \quad (7)$$

As above, P is an amount that decreases as the percentage x of scattered light in the optic media is larger, that is, as the opacity is stronger. Thus, the degree of opacity in the optic media is considered to be able to be represented by the ratio P between the brightness Bb of the fundus image photographed with the visible light and the brightness Bir of the fundus image photographed with the infrared light.

In the processing in S10, the CPU 201 acquires a transmittance of the crystalline lens according to the opacity degree P by referring to the lens transmittance database 207 (S10). The lens transmittance database 207 has stored lens transmittances of a plurality of examinees' eyes measured in advance in association with opacity degrees P of crystalline lenses. In the present embodiment, as described above, the lens transmittances stored in the lens transmittance database 207 are determined by use of fundus images of the same examinee's eye subjected to a cataract operation, photographed before and after the operation. The lens transmittance Tλ can be obtained by the following expression (8).

$$T\lambda = \frac{B\lambda}{R\lambda} \quad (8)$$

Bλ in the expression (8) indicates the brightness of the fundus image photographed by projecting a laser beam of a predetermined wavelength to the examinee's eye before the cataract operation (i.e., the examinee's eye with a crystalline lens having an opacity). Rλ indicates the brightness of the fundus image photographed by projecting the laser beam of the predetermined wavelength to the examinee's eye after the cataract operation (i.e., the examinee's eye with the crystalline lens from which the opacity has been removed). In the present embodiment, the brightness Bλ, of the fundus image before the cataract operation and the brightness Rλ of the fundus image after the cataract operation are normalized in a similar manner to in S7 and S8. It is to be noted that photographing the fundus image by the laser beam of the predetermined wavelength may be performed by any ophthalmic apparatus other than the ophthalmic apparatus 1 of the present embodiment.

Such an ophthalmic apparatus may be any apparatus including a light projecting optical system for projecting light of a predetermined wavelength to a fundus Er of an examinee's eye E and a light receiving optical system having a light receiving element for receiving light from the fundus resulting from the light projected from the light projecting optical system so as to photograph a fundus image based on a result of received light by the light receiving element. Further, the ophthalmic apparatus is not required to photograph a fundus image as long as it has a structure of acquiring the intensity of light from a fundus Er resulting from the light projected to the fundus Er.

In the present embodiment, when acquiring the lens transmittance from the lens transmittance database 207, the CPU 201 approximates the relation of (Tλ, P) about a plurality of examinees' eyes E stored in the lens transmittance database 207 to an approximate expression by use of a method for least squares. The CPU 201 substitutes the opacity degree P obtained in the processing in S9 into the approximate expression and acquires the lens transmittance. Not limited thereto, more than one combination of (Tλ, P) stored in the lens transmittance database 207 may be linearly interpolated to find the lens transmittance corresponding to the opacity degree P obtained in the processing in S9 from linear interpolation.

The CPU 201 then determines the fluorescence intensity of the auto-fluorescence image photographed in the processing S1 (S11). Firstly, the brightness Bf of each pixel included in the fundus image portion D of the auto-fluorescence image photographed in S1 is determined by the following expression (9):

$$Bfi = \frac{Lfi - Vf}{Uf - Vf} \qquad (9)$$

where i=(1, 2, ..., n).

In this expression, Lfi indicates a gradation value of one pixel included in the fundus image portion D of the auto-fluorescence image, a suffix i in Bfi and Lfi denotes a corresponding pixel in the fundus image portion D consisting of n pixels. Uf is an average value of the gradation values of the pixels in the image region of the fluorescence member 42a of the fluorescence standard sample 42 and Vf is an average value of the gradation values of the pixels in the image region of the black member 42b.

The gradation values of the auto-fluorescence image are different according to the photographing conditions of the ophthalmic apparatus 1. In the present embodiment, therefore, the brightness of a normalized image not depending on the photographing condition is found by the expression (9). Bfi is smaller than the fluorescence intensity Afi of the auto-fluorescence emitted from the fundus Er by a scattered amount by the opacity of the crystalline lens. Accordingly, the fluorescence intensity Afi in each pixel of the auto-fluorescence image can be expressed by the following expression (10) using the transmittance Tλ and coefficients Cd and Cs which will be mentioned later:

$$Afi = Bfi \times \frac{1}{T\lambda} \times Cd \times Cs \qquad (10)$$

wherein i=(1, 2, ..., n).

In this expression, the coefficient Cd is a coefficient to compensate the brightness (gradation value) of the fluorescence member 42a varying by a diopter correction position by the diopter correction means. The coefficient Cs is a coefficient to compensate fundus information such as the size of an eyeball of the examinee's eye E. The coefficient Cs may be set by the control part 200 to a coefficient value corresponding to the information input when an examiner inputs either one or both of a corneal curvature radius and an ocular axial length as well as a refractivity of the eye E. It is to be noted that the coefficients Cd and Cs are not essential and may be used appropriately selectively in view of acceptable accuracy.

In the present embodiment, as above, the CPU 201 computes the expression (10) to thereby perform the processing of correcting the fluorescence intensity of the auto-fluorescence image (in each pixel) according to the degree of opacity in the optic media.

Successively, the CPU 201 multiplies the fluorescence intensity of each pixel calculated in the processing in S11 by a predetermined coefficient to convert the fluorescence intensity into gradation information and outputs this information on the monitor 60 (S12). The monitor 60 displays thereon the auto-fluorescence image with corrected gradation value of each pixel. Accordingly, for example, the examiner can recognize a distribution state and an accumulation amount of the auto-fluorescence material from the auto-fluorescence image displayed on the monitor 60. At that time, a value of the opacity degree P or a value of the lens transmittance Tλ obtained in S9 or S10, may be output and displayed on the monitor 60. This enables the examiner to additionally recognize the degree of cataract. As an alternative, an average value of intensity of the auto-fluorescence determined by the expression (10) may be calculated by the CPU 201 and output on the monitor 60. This case makes it easier for the examiner to estimate a total accumulation amount of the auto-fluorescence material.

The CPU 201 then returns the position of the filter 31b and the laser beam emitted from the laser beam emitting part 11 to respective original states corresponding to those before execution of the fluorescence image photographing and analyzing processing (S13). To be concrete, the filter 31b is set on the optical axis L2. Further, the first laser source 11a is turned off and the second laser source 11b is turned on. Thus, the examiner can continue to photograph the auto-fluorescence image of the fundus Er. The CPU 201 terminates the fluorescence image photographing and analyzing processing.

As described above, the ophthalmic apparatus 1 of the present embodiment photographs or captures the fundus image in such a manner that the fundus reflection light (light from the fundus Er) resulting from the laser beam projected from the ophthalmic apparatus 1 to each point in a photographing range on the fundus Er is received by the light receiving element 25. In the ophthalmic apparatus 1, the degree of opacity in the optic media (the opacity degree P and the lens transmittance Tλ in the present embodiment) in the image data of the fundus image is analyzed from the gradation values indicating the intensity of the light from the fundus Er received by the light receiving element 25. As the opacity in the optic media of the eye E is stronger, the scattered amount of the laser beam to the fundus Er and the scattered amount of light from the fundus Er are respectively increased. Accordingly, as the opacity in the optic media is stronger, the intensity of the light received by the light receiving element 25 is lower. Thus, the intensity of the light received by the light receiving element 25 reflects the degree of opacity in the optic media. The ophthalmic apparatus 1 therefore can find the degree of opacity in optic media based on the intensity of reflection light reflected at each point on the fundus Er.

In a case of finding the degree of opacity of the optic media, there is conceived a method for finding it based on an observation result of an anterior segment of the eye E. For instance, an anterior segment image (transillumination image) of the eye E is photographed by an optical system for observing an anterior segment. Another conceivable method is to find the degree of opacity based on size and color density of the opacity captured in the anterior segment image.

In contrast, according to the ophthalmic apparatus 1 of the present embodiment, the degree of opacity in the optic media is analyzed based on the image data of the fundus image. Thus, the ophthalmic apparatus 1 can determine the degree of opacity in the optic media even if an optical system for observing the anterior segment is not provided.

Furthermore, examinees' eyes are individually different in ocular axial length, retinal shape, light reflectance of a retina, and others. Accordingly, even when the eyes E which are similar or equal in degree of opacity in the optic media are to be photographed, the intensity of light from respective fundus Er received by the light receiving element 25 varies by eye. Consequently, when the degree of opacity in the optic media is to be analyzed based on the intensity of reflection light reflected at each point on the fundus Er, it is considered that the reference indicating the degree of opacity may be different from eye to eye. If the reference indicating the degree of opacity is different from eye to eye, when the disease cases of different examinees' eyes are to be compared, a problem may occur that it is hard to refer to the degree of opacity in the optic media found in each examinee's eye.

In the ophthalmic apparatus 1 of the present embodiment, in contrast, the degree of opacity in the optic media is acquired based on the ratio between the brightness Bb of the fundus image photographed with the visible light (i.e., the intensity of the fundus reflection light resulting from the visible laser beam) and the brightness Bir of the fundus image photographed with the infrared light (i.e., the intensity of the fundus reflection light resulting from the infrared laser beam) (S9 and S10). It is conceived as mentioned above that the ratio between Bb and Bir is a value not depending on the individual differences among eyes of examinees and according to the degree of opacity in the optic media. Accordingly, it is possible to suppress an error due to the influence of the individual differences among examinees' eyes (e.g., ocular axial length, retinal shape, light reflectance of a retina) on the degree of opacity in the optic media determined by the ophthalmic apparatus 1. As a result, for example, when different eyes E are to be observed through the ophthalmic apparatus 1, the degree of opacity in the optic media of each eye E can be determined with the same reference.

Meanwhile, as mentioned above, the gradation value of image data of the fundus image is influenced by the photographing conditions of the ophthalmic apparatus 1 such as for example the light amount of a laser beam and the gain of the light receiving element 25. This is because the signal intensity of the received light signal output from the light receiving element 25 that receives the light from the fundus Er is influenced by the photographing conditions such as the light amount of a laser beam.

To avoid such a defect, the ophthalmic apparatus 1 of the present embodiment is configured such that Bb and Bir are respectively determined by normalizing the gradation values (Lb−Vb) and (Lir−Vir) of the fundus image portion D included in the photographed image by the gradation values (Ub−Vb) and (Uir−Vir) of the white member 41a. Bb and Bir are equivalent to the values obtained by normalizing the intensity of the fundus reflection light received by the light receiving element 25 by the intensity of light from the white member 41a received by the light receiving element 25. As described above, Bb and Bir are determined with suppressed errors due to the influence of the photographing conditions of the ophthalmic apparatus 1 as compared with the state before normalization. The degree of opacity in the optic media of the eye E is a value based on Bb and Bir, so that an analysis value of the degree of opacity in the optic media can be obtained with reduced errors due to the photographing conditions of the ophthalmic apparatus 1. Even when the same examinee's eye E undergoes photographing under different photographing conditions, for example, it is easy to obtain the same degree of opacity in the optic media.

Moreover, the ophthalmic apparatus 1 can acquire a transmittance of a crystalline lens corresponding to the opacity degree P by referring to the lens transmittance database 207. By the ophthalmic apparatus 1, therefore, the transmittance of the crystalline lens of the eye E can be obtained appropriately.

In addition, the lens transmittance Tλ stored in the lens transmittance database 207 is a value found by measuring the intensity of light from the fundus in each state; before and after a cataract operation. The ophthalmic apparatus 1 thus can acquire a correct transmittance of the crystalline lens from the lens transmittance database 207.

When the intensity of auto-fluorescence produced in the fundus is to be measured, if an optic media of an examinee's eye has opacity, a measurement value of the intensity of auto-fluorescence may be smaller than in the case where the optic media has no opacity. Accordingly, it is difficult to quantitatively determine the intensity (light amount) of auto-fluorescence produced in the fundus Er. Thus, for example, when the accumulation amount of auto-fluorescence material in the fundus of an examinee's eye having an opacity in an optic media is measured from the intensity of fluorescence received by the light receiving element, the accumulation amount of the auto-fluorescence material may be estimated to be smaller than actual.

In the present embodiment, in contrast, the fluorescence intensity of the auto-fluorescence is determined by adding the lens transmittance Tλ obtained by the control part 200 as a result of analysis of the degree of opacity in the optic media. This provides an advantageous effect that the intensity of auto-fluorescence produced in the fundus Er is easily quantatively determined while suppressing the influence of opacity of the optic media.

It is to be noted that algorithm (e.g., the expressions (1) to (10)) of the fluorescence image photographing and analyzing processing in the present embodiment can be changed appropriately. For instance, the processing of determining the lens transmittance Tλ by use of the lens transmittance database 207 may be omitted. In this case, for example, the fluorescence intensity of the auto-fluorescence image may be corrected by use of the opacity degree P instead of the lens transmittance Tλ, in the above expression (10).

This disclosure is explained above along the embodiments but is not limited thereto, and also may be embodied variously in other specific forms.

For instance, in the above embodiment, the ophthalmic apparatus 1 is explained as being configured to quantify the fluorescence intensity of fluorescence emitted from the auto-fluorescence material accumulated in the fundus Er according to the degree of opacity. As an alternative, the apparatus 1 is applicable to quantify the reflection intensity of the fundus reflection light. When the fundus is to be photographed by use of a fluorescence contrast agent, the apparatus 1 is also applicable to quantify the intensity of fluorescence produced from the fluorescence contrast agent according to the degree of opacity. As the fluorescence contrast agent, there may be used indocyanin green, fluorescein, and others.

The above embodiment explains the example in which the opacity degree P is determined by calculating the ratio between the brightness Bb of the fundus image photographed with the visible light and the brightness Bir of the fundus image photographed with the infrared light. However, the ophthalmic apparatus 1 does not always have to perform the processing of calculating the ratio and has only to acquire the opacity degree P corresponding to the ratio between the brightness Bb of the fundus image photographed with the visible light and the brightness Bir of the fundus image photographed with the infrared light. For instance, a table that stores opacities P associated with a plurality of combinations of Bb and Bir may be prepared in advance in the ophthalmic apparatus 1 so that the opacity degree P associated with Bb and Bir is obtained by referring to the table based on the Bb and Bir obtained by measurement of the examinee's eye E by the ophthalmic apparatus 1.

The above embodiment describes the example in which the ophthalmic apparatus 1 acquires, as the degree of opacity, the opacity degree P and the lens transmittance Tλ. However, the degree of opacity acquired by the ophthalmic apparatus 1 may be any information other than the above information. For instance, the ophthalmic apparatus 1 may be configured to acquire such an information as representing the degree of opacity at a plurality of evaluation levels (e.g. five levels).

In the above embodiment, the ophthalmic apparatus 1 is explained as a scanning laser ophthalmoscope. This disclosure may be applied to another ophthalmic apparatus configured to acquire the intensity of light from each point on a fundus. For instance, this disclosure may be applied to a fundus camera. This disclosure may also be embodied without including a structure for photographing a fundus image as long as it can obtain the intensity of light from a fundus resulting from the light projected on the fundus.

In a case where this disclosure is applied to the fundus camera, it may be arranged to photograph a fundus image to determine the degree of opacity in an optic media by sequentially irradiating a fundus Er with flash light beams different in wavelength band separately from the case of photographing an auto-fluorescence image of the fundus Er. When a color fundus image is to be photographed by a fundus camera, the control part 200 can determine the degree of opacity in an optic media by use of a single color fundus image. For instance, when the image data of the fundus image includes four color luminance information (e.g., luminance values) of R (red), G (green), B (blue), and IR (infrared), the degree of opacity in the optic media is determined by use of the luminance information of at least two colors thereof. For instance, when a luminance value of a first color component (e.g., a component B) of the color fundus image is substituted into Lb of the expression (1) and a luminance value of a second color component (e.g., a component R) different from the first color component is substituted into Lir of the expression (2), the apparatus can determine the degree of opacity in the optic media by use the algorithm in the above embodiment. At that time, Lb and Lir are values in the same range of the fundus and thus the degree of opacity in the optic media can be more appropriately determined.

The above embodiment describes the example in which the degree of opacity in the optic media is analyzed by use of two kinds of fundus images (the fundus image based on the fundus reflection light resulting from the visible laser beam and the fundus image based on the fundus reflection light resulting from the infrared laser beam) photographed by switching the wavelength of a laser beam to be projected to the fundus. However, it is not always necessary to photograph two kinds of fundus images. For instance, when an error due to individual differences among examinees' eyes is acceptable in association with the measurement accuracy, the degree of opacity can be determined by use of only either one of the two kinds of fundus images. In this case, for example, the RAM 203 stores in advance a fundus image of an examinee's eye having no opacity in an optic media (hereinafter, referred to as a "reference image") or an average gradation value of the fundus image obtained with a laser beam of a predetermined wavelength. When the ophthalmic apparatus 1 photographs a fundus image with a laser beam of a predetermined wavelength, the control part 200 is caused to determine a gradation value of the photographed fundus image. The ratio between the gradation value of the photographed fundus image and the gradation value of the reference image may be determined as an opacity degree P (one example of the degree of opacity).

The above embodiment explains the example in which the wavelength of a laser beam to be projected from the light projecting optical system 2 to the fundus is switched between a visible region and an infrared region in order to photograph two kinds of fundus images (the fundus image based on the fundus reflection light resulting from the visible laser beam and the fundus image based on the fundus reflection light resulting from the infrared laser beam). As an alternative, the laser beam in the visible region and the laser beam in the infrared region may be simultaneously output from the light projecting optical system 2 so that the ophthalmic apparatus 1 photographs two kinds of fundus images. In this case, for example, the rotary disc 31 may be provided with an infrared light transmission filter that transmits the light in an infrared region (fundus reflection light resulting from the first light) but blocks the light in a visible region (fundus reflection light resulting from the second light) and a visible light transmission filter that blocks the light in an infrared region but transmits the light in a visible region. In addition, the control part 200 switches between the infrared light transmission filter and the visible light transmission filter to be disposed on an optical path of the photographing optical system 3. Accordingly, the ophthalmic apparatus 1 can acquire two kinds of fundus images photographed with the laser beams having different wavelengths' based on a light receiving result of the light receiving element 25.

Figure 9:
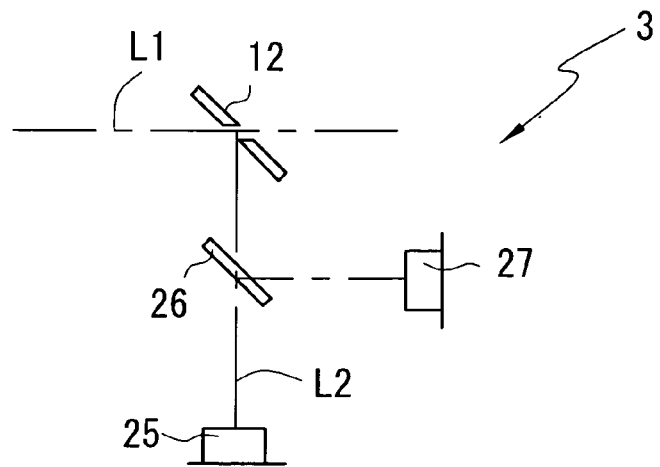
FIG. 9 is a schematic configuration view showing optical systems of a modified example of the present disclosure.

Furthermore, two kinds of fundus images to be acquired by the ophthalmic apparatus 1 when two kinds of laser beams having different wavelengths are simultaneously output from the light projecting optical system 2 may be photographed at the same time. For instance, as shown in FIG. 9, a dichroic mirror 26 and a light receiving element 27 may be provided in the photographing optical system 3. The dichroic mirror 26 is arranged on the optical axis L2 of the photographing optical system 3 to reflect the light in the infrared region but transmits the light in the visible region. Therefore, when two kinds of laser beams are to be simultaneously output from the light projecting optical system 2, the dichroic mirror 26 separates the fundus reflection light resulting from the infrared light and the fundus reflection light resulting from the visible light. The light receiving element 27 is placed on an optical axis on a reflection side of the dichroic mirror 26 and has sensitivity to at least light of wavelengths in an infrared region. The ophthalmic apparatus 1 including such optical systems can acquire two kinds of fundus images simultaneously photographed by the light receiving element 25 and the light receiving element 27 respectively. There is no difference due to temporal changes of the eye E (e.g., positional displacement between images due to involuntary eye movements) between the simultaneously photographed two kinds of fundus images. Thus, the degree of opacity in the optic media to be determined by the ophthalmic apparatus 1 has less errors resulting from the temporal changes of the eye E.

In the above embodiment, the example is explained in which the image to be used for analysis of the degree of opacity in the optic media is photographed with the fundus reflection light of the laser beam. This photographing may be made by fluorescence produced in the fundus. In this case, it is preferable to make the fluorescence, not the fundus reflection light, enter the light receiving element of the ophthalmic apparatus. Accordingly, for example, when the image used for analysis of the degree of opacity in the optic media is to be photographed, the rotary disc 31 in the above embodiment may be provided with a filter having a spectral property that allows fluorescence from the fundus Er to pass but blocks the fundus reflection light.

The above embodiment describes the example in which the infrared laser beam and the visible laser beam are projected to the eye E to determine the degree of opacity in the optic media. As an alternative, a laser beam of a different wavelength from the above may be projected to determine the degree of opacity in the optic media. However, since the light of wavelengths in the ultraviolet region is likely to be absorbed by a cornea, the light in the visible region or the light having a longer wavelength than in the visible region is preferably projected. As the two kinds of laser beams are more different in wavelength from each other, the laser beams have more different effects on scattering by opacity. This enables easy and accurate determination of the degree of opacity (the opacity degree P and the lens transmittance T$\lambda$ in the present embodiment). Therefore, two kinds of laser beams are preferably combined so that one is the light in a region at a boundary between a visible region and an ultraviolet region (the light having a wavelength of about 380 nm) and the other is the light in an infrared region (the light having a wavelength of about 790 nm).

In the above embodiment, Vb used in the expression (1) and Vir used in the expression (2) are determined respectively from the gradation values of the black members 41b and 42b in the photographed image. In an alternative, the black members 41b and 42b are not provided and Vb and Vir are determined from the gradation values consisting of the received light signals of the light receiving element 25 when the laser beam is turned off.

The above embodiment shows the example in which the degree of opacity in the optic media (the opacity degree P and the lens transmittance Tλ) is determined by use of the ratio between the brightness Bb and the brightness Bir (that is, the ratio between the intensity of the fundus reflection light by the infrared laser beam and the intensity of the fundus reflection light by the visible laser beam). However, the degree of opacity in the optic media may be determined by another computation. For instance, the degree of opacity in the optic media may be determined by the difference between the brightness Bb and the brightness Bir.

In the above embodiment, either one of the standard samples 41 and 42 is always placed in the scanning range of the laser beam, but is not limited thereto. For instance, in a photographing mode where FAF photographing is not conducted, e.g., in the manual mode, both the standard samples 41 and 42 may be retracted out of the scanning range of the laser beam. Accordingly, in the photographing mode needing no analysis of fluorescence intensity, the standard samples 41 and 42 are not photographed and thus the information of a fundus which is hidden behind the standard samples 41 and 42 during FAF photographing can be obtained.

The above embodiment describes the example in which one of the reflection standard sample 41 and the fluorescence standard sample 42 is placed between the concave mirror 21 and the mirror 20, but the standard sample may be placed in another place. For instance, a mirror switchable in position by a drive mechanism is placed between the perforated mirror 12 and the lens 13. While the mirror is inserted in place, the standard sample 41 or 42 is disposed on the optical path of a laser beam reflected by the mirror. In this case, the standard sample 41 and 42 is photographed while the mirror is inserted, whereas the fundus image is photographed while the mirror is retracted. Thus, the gradation values Lb and Lir of the fundus image and the gradation values (Ub, Vb) and (Uir, Vir) of the standard sample 41 or 42 are preferably determined from separately photographed images.

The above embodiment explains that the fundus image including both the fundus image portion D and the standard sample 41 or 42 is displayed on the monitor 60. Alternatively, the monitor 60 may be caused to display a range except the standard sample 41 or 42.

In the above embodiment, the reflection standard sample 41 including the white member 41a and the black member 41b in order to calculate the brightness Bb of the fundus image photographed with the visible light and the brightness Bir of the fundus image photographed with the infrared light. Alternatively, the reflection standard member 41 may be provided with an intermediate member having a reflectance intermediate between the reflectances of the white member 41a and the black member 41b.

For instance, for a strongly opaque optic media, the light amount of the laser beam and the gain of the light receiving element 25 can be demanded to be increased in order to photograph a fundus image with sufficient brightness. At that time, the average gradation values Ub and Uir in the white member 41a are likely to become a saturated level (255 in the case of the gradation values ranging from 0 to 255). Vb and Vir of the black member 41b are likely to become a zero level (0 in the case of the gradation values ranging from 0 to 255). When Ub and Uir are at the saturated level or Vb and Vir are at the zero level, it is conceived that the intensity of the reflection light from the reflection standard sample 41 is not reflected correctly in the values (Ub, Vb) or (Uir, Vir). In this case, therefore, Bb or Bir may result in an incorrect value (see the expressions (1) and (2)).

To avoid this defect, the reflection standard sample 41 is additionally provided with an intermediate member having a reflectance intermediate between those of the white member 41a and the black member 41b. For instance, in a case where the reflectances of the laser beams in the white member 41a and the black member 41b are respectively 99% and 1%, a first intermediate member of a 64% reflectance and a second intermediate member of a 25% reflectance are provided. In this case, Bb and Bir may be calculated by substituting an average gradation value of the first intermediate member by irradiation of each laser beam into Ub or Uir and also substituting an average gradation value of the second intermediate member by irradiation of each laser beam into Vb or Vir.

The processing by the CPU 201 to determine the brightnesses Bb and Bir of the fundus images by use of the gradation values of the intermediate member(s) may be performed in response to a predetermined input operation to the operation part 50 by the examiner. Furthermore, for instance, in the processings in S8 and S9 of the fluorescence image photographing and analyzing process, the CPU 201 may be caused to determine whether or not the light amount of the laser beam and the gain of the light receiving element 25 are higher than respective predetermined thresholds. In this case, if the CPU 201 determines that they are higher than the predetermined thresholds, Bb and Bir is determined by use of the gradation value(s) of the intermediate member(s).

In the processings of S8 and S9 of the fluorescence image photographing and analyzing processing, the CPU 201 may be caused to determine whether the gradation value of the white member 41a is at the saturated level or not, or, whether the gradation value of the black member 41b is at the zero level or not. If the CPU 201 determines that the gradation value of the white member 41a is at the saturated level or that the gradation value of the black member 41b is at the zero level, Bb and Bir is determined by use of the gradation value of the intermediate member.

In the above embodiment, the lens transmittance database 207 is explained as storing the lens transmittances Tλ of more than one examinee's eye in association with the opacity degrees P, but not limited thereto. For example, the lens transmittance database 207 may store, as information related to a transmittance of an optic media, a value of an opacity degree P0 of an examinee's eye (a normal eye) with no opacity in a crystalline lens (i.e., a constant J in the expression (7) in the above embodiment). In this case, the control part 200 can obtain a transmittance of an optic media as a value calculated by dividing the opacity degree P obtained by the expression (7) by the opacity degree P0 stored in the lens transmittance database 207. Herein, FIG. 10 shows an opacity degree and a transmittance of an optic media of a model eye (a schematic eye) having a predetermined transmittance, measured by the ophthalmic apparatus 1 using the opacity degree P0.

In each measurement, the results of which are shown in FIG. 10, a cloudy liquid that has a wavelength transmission property close to a cataract eye is placed in front of the model eye to make the model eye simulate the cataract eye. The fundus of the model eye has a light reflection property (a light absorbing property) similar to the fundus of an examinee's eye. In FIG. 10, "Transmittance" in a vertical axis is defined by assuming that full transmission of light is "1" and no transmission of light is "0". Further, a smaller number in "Data Number" indicates data of the measurement using a liquid more strongly opacified in front of the model eye. The data No. 5 indicates a result of the measurement using a liquid not opacified. As shown in FIG. 10, the opacity degrees (measurement values) measured by the ophthalmic apparatus 1 are smaller values than 1 irrespective of the presence/absence of opacity in each optic media. This is because the visible laser beam is more likely to be absorbed by the fundus than the infrared laser beam. In the case where the opacity degree (measurement value) is divided by P0 stored in the lens transmittance database 207, as shown in FIG. 10, a transmittance (measurement value) having less error with respect to an actual transmittance (set value) of the model eye is measured by the ophthalmic apparatus 1.

The lens transmittance database 207 may store for example the brightnesses Bb and Bir in association with the lens transmittances Tλ. Further, the lens transmittance database 207 may store fundus images of each of examinees' eyes captured before and after cataract operation. In this case, every time when the control part 200 refers to the lens transmittance database, the control part 200 determines the lens transmittance Tλ from the fundus image in the lens transmittance database 207 corresponding to the opacity degree P and others. The lens transmittance database 207 may also be a storage device separate from the ophthalmic apparatus 1.

In the ophthalmic apparatus 1, furthermore, a diaphragm (an artificial pupil) may be provided between the concave mirror 21 and an examinee's eye E. This makes it easy to allow a uniform amount of laser light to enter each of examinees' eyes E irrespective of pupil diameters of the eyes. Thus, the auto-fluorescence image photographed by the ophthalmic apparatus 1 can be easily compared with the auto-fluorescence image of another examinee's eye.

The above embodiment explains the example in which the control part 200 acquires the intensity information (the brightness Bir in the above embodiment) of the light from the fundus resulting from the first light and the intensity information (the brightness Bb in the above embodiment) of the light from the fundus resulting from the second light based on the gradation values of pixels included in the entire range of the fundus image portion D. As an alternative, the control part 200 may acquire the intensity information of the light from the fundus based on the gradation values of pixels included in a part of the fundus image portion D. This part of the fundus image portion D may be set based on a range specifying information acquired in advance by the apparatus. The range specifying information may be selected from for example the information indicating a range on the fundus image portion D designated by an examiner through the operation part 50 and others or the information indicating a fixed range determined in advance.

Figure 11:
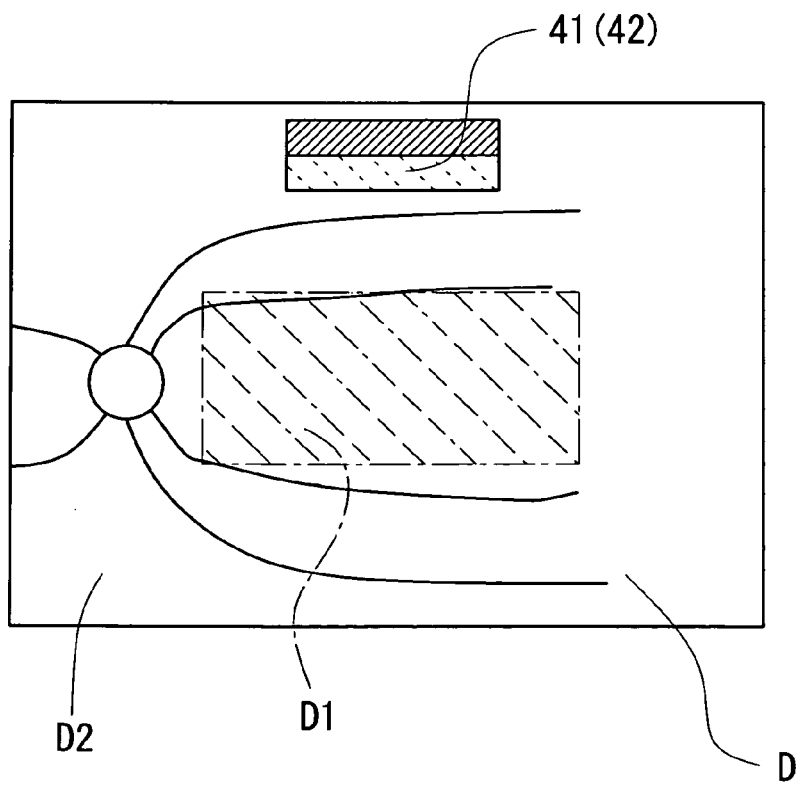
FIG. 11 is a schematic diagram showing a central region of a photographing optical system in a fundus image.

Meanwhile, the inventors found that, as the range of the fundus image portion D in which the intensity information is acquired is clearer, the degree of opacity in an optic media could be more properly by the processings in the above embodiment. Accordingly, the control part 200 may set a central region D1 (see FIG. 11) in the fundus image portion D as the range to acquire the intensity information. In this case, in the fundus image photographed with the diopter adjusted so that the fundus Er and the light receiving element 25 are in a conjugated positional relation, an image region closer to the central region of the photographing optical system 3 is less influenced by the optical system that photographs the image (the photographing optical system 3) and an aberration due to the examinee's eye and others, resulting in a clearer image. On the other hand, a peripheral region D2 in the fundus image portion D may be largely influenced by aberration, resulting in an unclear image.

The range to acquire the intensity information has only to be set to a region likely to suppress the influence of the aberration and others in the fundus image, and does not always have to be set in the vicinity of the photographing center. For instance, the control part 200 may be configured to obtain the information related to the optical systems for photographing an image (intensity information, aberration information, etc.) and the information related to the examinee's eye (information related to refractive power and ocular axial length, aberration information, etc.), determines the region of the fundus image in which a clear image is formed, and acquires the intensity information from the determined region.

In each of the above embodiments, the ophthalmic apparatus 1 is explained as analyzing the degree of opacity in an optic media, but is not limited thereto. For instance, it may be arranged to transmit two kinds of fundus images different in wavelength of light used for photographing and identical in photographing range to a generally used computer (e.g., a personal computer), and allow this computer to execute image processing to determine the degree of opacity in the optic media. In this case, the computer may install, on a hard disc or the like, an analysis program to cause a computer processor to execute the processing in S7 to S9 or S7 to S10 in the fluorescence image photographing and analyzing processing which is performed by the ophthalmic apparatus 1 in the above embodiment as a program to determine the degree of opacity in the optic media. In this case, the computer can determine the degree of opacity in the optic media in a similar manner in the ophthalmic apparatus 1 of the above embodiment.

In a computer to which an auto-fluorescence image photographed in the same photographing range as that of the image used for determining the degree of opacity in the optic media has been transmitted (has acquired) in advance, the processing in S11 of the fluorescence image photographing and analyzing processing may be performed after execution of the processing corresponding to S7 to S9 or S7 to S10. In this case, the fluorescence intensity of auto-fluorescence incorporating the degree of opacity in the optic media can be obtained.

As explained above, by correcting the intensity of fluorescence from the fundus by use of the degree of opacity in the optic media, the ophthalmic apparatus 1 can appropriately obtain the intensity of fluorescence. In the above embodiment, the degree of opacity in the optic media is analyzed based on the intensity information related to the intensity of light emitted from the fundus according to the light projected to the fundus from the light projecting optical system. However, the degree of opacity in the optic media used for correcting the fluorescence intensity may be determined by a manner other than the analysis using the above intensity information.

For instance, the degree of opacity in the optic media is acquired in such a manner that light is projected to an examinee's eye, the light returning from the optic media of the examinee's eye or a site closer to the fundus is received by the light receiving element, the degree of opacity is obtained based on a signal output from the light receiving element. For instance, it may be acquired by analysis of cross-section information of an examinee's eye including an optic media.

The cross-section information of the examinee's eye may be acquired by a cross-section imaging apparatus configured to cause a detector (a light receiving element) to receive reflection light from the optic media of the examinee's eye and obtain a cross-section image of the eye based on a received light signal output from the detector. This cross-section imaging apparatus includes for example a light projecting optical system for projecting light from a light source to the examinee's eye and forming an optical cross-section in the optic media and a light receiving optical system for detecting, through the detector, the light including scattered light (and reflected light) scattered (and reflected) in the optic media on the optical cross-section.

The cross section information of the examinee's eye may be raw data by a signal output from the detector, a cross section image produced by processing of the signal, or data generated by image processing of the cross section image. In this case, the cross section information on a plurality of different optical cross sections from each other is analyzed, so that the degree of opacity in the optic media can be obtained at each site in the optic media. For the details, refer to e.g. JP-A-2003-111731. Examples of the cross-section imaging apparatus are a Scheimpflug camera, an optical coherence tomography (OCT) device, and others. The cross-section imaging apparatus may be an apparatus provided in a separate casing from or in the same casing as the ophthalmic apparatus for correcting the intensity of auto-fluorescence using the degree of opacity in the optic media. In the case of the apparatus provided in the same casing as the ophthalmic apparatus, operations of both apparatuses are controlled by a single control part.

The degree of opacity in an optic media may be determined by analysis of a transillumination image of an examinee's eye. The transillumination image can be obtained by use of an anterior segment imaging apparatus configured to receive reflection light from a fundus of an examinee's eye through an imaging apparatus (a light receiving element) placed in a position conjugate with an optic media (or its vicinity). The transillumination image is thus produced based on a signal from the imaging apparatus. In this case, analysis of image information of an opaque or cloudy portion of the transillumination image enables acquiring the degree of opacity in the optic media at each site in the optic media. The anterior segment imaging apparatus may be provided in a casing separate from or in the same casing as the ophthalmic apparatus configured to correct the intensity of auto-fluorescence. In the case of the apparatus provided in the same casing as the ophthalmic apparatus, operations of both the apparatuses may also be controlled by a single control part.

The present disclosure is explained in the specific examples referring to the drawings but is not limited thereto. This disclosure may be modified or corrected without departing from the scope defined by the accompanying claims.

What is claimed is:

1. An ophthalmic apparatus including:
a light projecting optical system to project light to each point on a fundus of an examinee's eye;
a light receiving optical system including a light receiving element to receive light from the fundus emitted from each point on the fundus resulting from the light projected from the light projecting optical system; and
a controller for controlling the ophthalmic apparatus, wherein the controller is configured to:
acquire intensity information representing intensity of the light from the fundus corresponding to each point on the fundus based on a result of received light of the light receiving element; and
analyze a degree of opacity in an optic media of the examinee's eye based on the intensity information.

2. The ophthalmic apparatus according to claim 1, wherein the light projecting optical system is arranged to project first light of a first wavelength and second light of a second wavelength shorter than the first wavelength to the fundus of the examinee's eye, and
the controller is configured to:
acquire first intensity information that is the intensity information of the light from the fundus resulting from the first light and second intensity information that is the intensity information of the light from the fundus resulting from the second light, and
obtain the degree of opacity in the optic media of the examinee's eye by use of a ratio between the intensity of the light from the fundus resulting from the first light indicated by the first intensity information and the intensity of the light from the fundus resulting from the second light indicated by the second intensity information.

3. The ophthalmic apparatus according to claim 1, wherein the controller acquires the intensity information indicating the intensity of the light from the fundus corresponding to each point on the fundus based on light in a central region of the light receiving optical system of the light emitted from the fundus and received by the light receiving element.

4. The ophthalmic apparatus according to claim 1, wherein the controller acquires a transmittance of the optic media corresponding to the intensity information by use of a database storing information related to transmittances of optic media of a plurality of examinees' eyes.

5. The ophthalmic apparatus according to claim 4, wherein the database stores a transmittance of a crystalline lens of the examinee's eye, the transmittance being a value obtained in such a manner that, based on intensity of the light from the fundus of the eye received by the receiving element in each of a state of the crystalline lens with opacity before cataract surgery and a state of the crystalline lens after the cataract surgery, a value indicating the intensity before cataract surgery is divided by a value indicating the intensity after the cataract surgery.

6. The ophthalmic apparatus according to claim 1, wherein a reference part is placed in front of the examinee's eye to emit reference light when the reference part is irradiated by the light from the light projecting optical system,
the light receiving optical system receives the reference light from the reference part by the light receiving element, wherein
the controller is configured to:
normalize the intensity of the light from the fundus indicated by the intensity information, based on intensity of the reference light emitted from the reference part and received by the light receiving element, and
analyze the degree of opacity in the optic media of the examinee's eye based on the normalized intensity of the light from the fundus.

7. The ophthalmic apparatus according to claim 1, wherein the light projecting optical system projects light to the fundus of the examinee's eye to excite a fluorescent material existing in the fundus of the eye and emit fluorescence, and the controller corrects intensity of the fluorescence emitted from the fundus and received by the light receiving element according to the analyzed degree of opacity in the optic media of the eye.

8. An analysis program to be executed in an analysis device to analyze a state of an examinee's eye by use of intensity information indicating intensity of light from a fundus of the eye resulting from light projected to each site on the fundus,
wherein the program is executed by a processor of the analysis device to cause the analysis device to execute an analysis step of analyzing a degree of opacity in an optic media of the eye based on the intensity information.

9. A method for acquiring a degree of opacity in an optic media, the method including:
a first intensity information acquiring step of acquiring first intensity information of light emitted from each site on a fundus of an examinee's eye by projecting first light of a first wavelength to each site on the fundus, the first intensity information being acquired based on a signal from a light receiving element that receives the light from the fundus;
a second intensity information acquiring step of acquiring second intensity information of light emitted from each site on the fundus by projecting second light having a shorter wavelength than the first wavelength to each site on the fundus, the second intensity information being acquired based on a signal from the light receiving element; and
an opacity acquiring step of acquiring the degree of opacity in the optic media of the examinee's eye by use of a ratio between intensity of the light from the fundus resulting from the first light indicated by the first intensity information and intensity of the light from the fundus resulting from the second light indicated by the second intensity information.

10. A method for acquiring fluorescence intensity, the method including:
a first light projecting and receiving step of projecting light to an examinee's eye and receiving light returning from an optic media of the eye or a site closer to a fundus of the eye than the optic media through a first light receiving element;
a second light projecting and receiving step of projecting excitation light to the fundus of the eye to excite a fluorescent material existing in the fundus and emit fluorescence, and receiving the light through a second light receiving element that is the same as or separate from the first light receiving element;
an opacity acquiring step of acquiring a degree of opacity in the optic media of the eye based on a signal output from the first light receiving element that receives the returned light in the first light projecting and receiving step;
a fluorescence intensity acquiring step of acquiring intensity of the fluorescence from the fundus of the eye based on a signal output from the second light receiving element that receives the fluorescence in the second light projecting and receiving step; and
a correcting step of correcting the intensity of the fluorescence obtained in the fluorescence intensity acquiring step by use of the degree of opacity in the optic media of the eye acquired in the opacity acquiring step.

* * * * *